United States Patent [19]

Warrell, Jr. et al.

[11] Patent Number: 4,529,593

[45] Date of Patent: Jul. 16, 1985

[54] USE OF GALLIUM SALTS TO TREAT DISORDERS OF CALCIUM HOMEOSTASIS

[75] Inventors: Raymond P. Warrell, Jr.; Richard S. Bockman, both of New York, N.Y.

[73] Assignee: Sloan-Kettering Institute for Cancer Research, New York, N.Y.

[21] Appl. No.: 622,726

[22] Filed: Jun. 20, 1984

Related U.S. Application Data

[63] Continuation-in-part of Ser. No. 436,133, Oct. 22, 1982, abandoned.

[51] Int. Cl.³ ............................................. A61K 33/00
[52] U.S. Cl. .................................................... 424/127
[58] Field of Search ......................................... 424/127

[56] References Cited

PUBLICATIONS

Warrell et al., J. Clin. Invest., vol. 73, May 1984, pp. 1487–1490.

Merck Index, 9th (1976), pp. 560–566.

Primary Examiner—Stanley J. Friedman
Attorney, Agent, or Firm—Felfe & Lynch

[57] ABSTRACT

The present invention comprises a method of preventing or treating a disorder associated with accelerated loss of calcium from bone in a human individual comprising administering to the individual a pharmaceutically acceptable gallium compound. Of especial importance among the disorders which may be thus prevented or treated are hypercalcemia, accelerated bone loss associated with osteopenia, osteoporosis, bone metastasis due to malignant tumors, and hyperparathyroidism. In the method of the present invention gallium compounds may be administered by any and all routes.

Although all biocompatible, soluble compounds of gallium may be used in the present invention, gallium nitrate is preferred, most preferably in a pharmaceutically acceptable carrier.

24 Claims, No Drawings

USE OF GALLIUM SALTS TO TREAT DISORDERS OF CALCIUM HOMEOSTASIS

This application is a continuation-in-part of application Ser. No. 436,133, now abandoned.

This invention concerns the use of gallium compounds to treat disorders associated with calcium loss from bone.

BACKGROUND

Loss of bone mass (osteopenia or osteoporosis) and accelerated loss of calcium from bone are major causes of medical illness. Increased bone resorption is commonly associated with many different diseases. These problems affect millions of persons in the U.S. alone. Examples of disorders due to increased bone resorption include: (a) Osteoporosis (loss of bone mass)—a major source of morbidity producing hip and vertebral fractures in elderly, post-menopausal women; (b) hypercalcemia (increased blood calcium concentrations)—a problem which occurs frequently in patients with hyperparathyroidism or cancer which can produce kidney failure, coma and death if not treated; (c) bone metastasis (spread of cancer cells into bone). In the absence of effective antitumor therapy (and this problem frequently afflicts persons who have proved resistant to anticancer therapy), cancer cells progressively erode the bone causing fractures and extreme pain. Clearly, a drug which could directly strengthen bone tissue and decrease bone resorption would be highly desirable.

A variety of treatments have been utilized to treat these various disorders (e.g. fluorides and estrogens for osteoporosis; intravenous fluids, diuretics, phosphates, and mithramycin for hypercalcemia; radiation treatments for bone metastases if the disease is not extensive). Each of these treatments suffers from certain disadvantages such as excessive toxicity, production of disordered bone growth, or weak activity.

Accordingly, a search has been undertaken to discover agents which inhibit calcium resorption from bone.

Gallium is a metal which belongs to the Group IIIa elements of the periodic table. By mechanisms which are still uncertain, radioactive gallium salts are known to accumulate in certain tumors (Dudley H. C. et al, Radiology, 50: 571, (1950). 67-Gallium citrate is currently used for diagnostic purposes in patients with bone infections and malignant diseases (McCaffrey J. A. et al, AM J Med 60: 523, 1976; Hoffer, P, J Nuc Med 21: 394, (1980)). In 1952, King et al (Arch. Int. Med. 90:785 (1952)) first showed that injections of highly radioactive gallium caused tumor regression in cancer patients. Non-radioactive salts of gallium and other Group IIIa metals were first evaluated for their anticancer activity in 1971 (Hart, M. M., Adamson R. H. et al, Proc Nat Acad Sci (USA) 68:1623, 1971; Hart, M. M., Smith C. F., et al, J Nat Cancer Inst 47:1121, (1971)). Gallium was found to be the most potent and least toxic element for reducing the size of animal tumors. The anionic component (i.e. whether the salt was a nitrate or a chloride) made no significant difference with respect to the direct anticancer action (Adamson, R. H. et al, Cancer Chemother Rep 59:599, (1975)). After completing preclinical toxicologic studies, gallium nitrate entered into clinical trials as a cytotoxic anticancer agent in 1976. U.S. Pat. No. 4,303,636 discloses a method of cancer treatment which uses radioactive 67-gallium, as a cytotoxic agent.

It is the use of gallium as an inhibitor of calcium resorption from bone that is the subject of the present invention.

SUMMARY OF THE INVENTION

It is a principal object of the present invention to provide a method for regulating resorption of calcium from bone.

It is another principal object of the present invention to provide a method of treating disorders associated with excessive loss of calcium from bone.

It is another object of the present invention to provide a method of preventing and treating hypercalcemia associated with cancer or hyperparathyroidism, two of the more common causes.

It is an important object of the present invention to provide a method of treating or preventing osteopenia or osteoporosis due to calcium resorption from bone. Factors which may be associated with osteopenia or osteoporosis include aging (especially in women), surgical castration, immobilization, and other causes.

It is a further object of the present invention to provide a method for the treatment or prevention of accelerated calcium loss from bone and bone destruction caused by direct invasion of bone by malignant tumors or by the secretion of bone-resorbing factors by cancer cells.

It is a further object of the present invention to provide a method for the treatment or prevention of accelerated calcium loss from bone, osteoporosis, osteopenia, and other diseases associated with increased bone resorption in animals.

It is further object of the present invention to provide a method of inhibiting release of calcium from cultured bones.

It is a further object of the present invention to provide a method of administering gallium salts in in amounts effective in treatment of both acute and chronic hypercalcemia.

It is a special object of the present invention to provide a method for treatment or prevention of accelerated calcium loss from bone due to periodontal disease.

In accordance with these objectives, the present invention comprises the pharmacologic use in humans and animals of any and all pharmaceutically acceptable non-radioactive gallium salts in non-nephrotoxic amounts to inhibit resorption of calcium from bone in patients with hypercalcemia, bone fragility or other disorders associated with abnormally increased calcium resorption.

A method of preventing or treating a disorder associated with extensive loss of calcium from bone in humans comprising administering to the individual a pharmaceutically acceptable gallium compound is disclosed. Of especial importance among the disorders which may be thus prevented or treated are hypercalcemia, osteopenia, osteoporosis, bone destruction due to metastasis from malignant tumors, and hyperparathyroidism. In the method of the present invention gallium compounds are preferably administered by intravenous subcutaneous or intramuscular injection including continuous infusion preferably in amounts from 10–400 mg/sqm/day whereby plasma gallium concentrations are maintained at about 0.9–2.0 ug/ml. The gallium compounds of the present invention also may be administered orally, sub-lingually, per rectum or transdermally, preferably in doses of 0.5 to 20 grams per day. Although all biocompatible, soluble compounds of gallium may be used in the present invention, gallium nitrate is preferred, most preferably in a pharmaceutically acceptable carrier. Preferred carriers are suitably buffered aqueous solutions, for example phosphate buffered saline or citrate buffers.

DETAILED DESCRIPTION

The present invention comprises a method of administering gallium salts, preferably gallium nitrate, along with a pharmaceutically acceptable carrier in non-nephrotoxic amounts to patients with hypercalcemia due to resorption of calcium from bone. Gallium salts which may be employed are those which are physiologically acceptable including nitrate, citrate, halide, preferably chloride, carbonate, acetate, tartrate, oxalate, oxide or hydrated oxide. It is to be understood that the active therapeutic agent is the gallium ion and, that therefore the choice of an ion may be determined by such factors as commercial accessibility, solubility characteristics, and mode of administration.

The gallium salt may be administered orally, sub-lingually, intramuscularly, subcutaneously, intravenously, transdermally or per rectum. The anticalcium effect of gallium salts is schedule-related (i.e. prolonged exposure to lower concentrations produces greater inhibition of bone resorption than short treatment with high doses). By example, in the preferred embodiment of the present invention, gallium nitrate for the treatment of cancer-related hypercalcemia is administered by continuous infusion for several days, followed by chronic treatment to prevent recurrence.

In the treatment of loss of calcium from bone due to periodontal disease the gallium compound may administered topically in an intra-oral formulation comprising, for example, a highly concentrated rinse, gel, or other pharmaceutically acceptable carrier for the local treatment of periodontal disease.

Pre-clinical Studies with Gallium Nitrate

A. GALLIUM EFFECTS ON WHOLE BONES IN VITRO.

Summary: Calcium releases from rat bones can be stimulated by various natural substances, including parathyroid hormone (PTH) and also by a factor derived from cancer cells which is similar to osteoclast activating factor ("OAF", a lymphokine). Gallium nitrate inhibits calcium release induced by both of these substances. The degree of inhibition was both time- and dose-dependent.

Experimental Data

The effects of gallium nitrate on bone resorption in vitro were studied using explants of fetal rat bones (Bockman, R. S. and Repo, M. A., J Exp Med 154:529, 1981). Pregnant rats were injected with 0.2–0.4 mCi of 45-CaCl2 on the 18th day of gestation. After 2 days of bone mineralization in utero, the radii and ulnae of fetal rats were explanted and placed on stainless steel rafts in BGJ media. Calcium releases from bone was stimulated by the addition of bovine PTH (2.0 microM, final concentration) or a lymphokine (OAF) preparation (10% of final volume). Gallium nitrate was added to the culture media at final concentration of 1, 5 and 10 mcg/ml simultaneously with—and 18 or 48 hours prior to—the addition of the bone-resorbing factors. After 48 hours of exposure to lymphokine or PTH, calcium release was determined by counting the supernatant media in a liquid scintillation counter. Data were expressed as the ratio of calcium release in counts per minute (cpm) of the experimental bone (treated or untreated with gallium nitrate and a resorbing factor) to cpm release by a paired control bone (treated or untreated with gallium nitrate) [cpm experimental/cpm control=E/C] Forty-nine bones were used to establish control values; 4–22 bones were used to obtain each of the experimental points.

The inhibitory effect of gallium nitrate upon bone resorption was found to be time-dependent. Addition of gallium nitrate (10 mcg/ml) simultaneously with (time 0), or 18 hrs preceeding the addition of PTH or lymphokine, decreased 45-Ca++ release relative to control bones incubated with lymphokine only, but the reduction was not statistically significant. However pre-incubation of bones for 48 hours preceeding the addition of lymphokine caused a highly significant reduction in lymphokine-induced 45-Ca++ release.

The inhibitory effects of gallium on PTH- or lymphokine-stimulated bone resorption was also found to be dose-dependent. After 48 hrs of preincubation, 1 mcg/ml of gallium nitrate caused no significant change in 45-Ca++ release after stimulation by PTH or lymphokine. However, significant and dose-related reductions in 45-Ca++ release were observed using concentrations of 5 and 10 mcg/ml of gallium nitrate, P less than 0.025.

B. EFFECTS OF GALLIUM UPON BONE CELLS.

Summary: Prior work (Warrell, R. P. Jr, Coonley, C. J. et al, Cancer 51:1982, (1983). Adamson, R. H. et al, Cancer Chemother Rep 59:599, (1975)) has established that gallium has modest anticancer activity against certain animal and human tumors. Other anticancer drugs, specifically a drug called mithramycin, can also reduce blood calcium levels. However, mithramycin causes this effect by directly killing bone cells (Minkin, C, Calcif Tissue Int 13:249, 1973). Therefore, the anti-calcium effect could be non-specifically related to lethal effects on both normal and cancerous cells.

Several experiments were performed to determine whether gallium was toxic to bone cells, and thus whether its anti-calcium effect was non-specifically related to lethal cellular effects. The results showed: (1) that pharmacologic concentrations of gallium do not cause lethal toxicity to bone cells; and (2) that the mechanism whereby gallium inhibits bone resorption is clearly different from mithramycin.

Experimental Data: Mithramycin causes considerable loss of bone cells (particularly osteoclasts) number after comparatively brief exposure (Minkin, C, Calcif Tissue Int 13:249, 1973; R. S. Bockman, unpublished observations). Samples of cultured rat bones used in experiments previously described herein were fixed, decalcified and stained with hematoxylin and eosin. Histologic sections were examined by light microscopy. By comparison with mithramycin-treated bones, bones exposed to pharmacologic concentrations of gallium for 72 hrs showed normal cellular components. Moreover, no differences in bone cell morphology were noted relative to untreated control bones. Specifically, both osteoclast number and size were similar in treated and untreated bones.

Furthermore, gallium treatment alone (i.e., without added PTH or lymphokine as in the preceding experiments) did not have any effect on 45-Ca++ release compared to control bones not exposed to gallium.

These data also indicate that the drug caused no cytotoxic effect on bone.

It has previously been shown that normal metabolism of fetal rat bones is associated with prostaglandin (PGE2) production in the basal state. In addition, PGE2 production can be markedly stimulated by lymphokine preparations that contain OAF (Bockman, R. S. and Repo, M. A., J Exp Med 154:529, 1981). When PGE2 release from explanted bones that had been exposed to gallium nitrate (10 mcg/ml) for 24–48 h was examined, no change in PGE2 over control (non-treated) bones was observed. No increase in bone calcium release (measured as 45-Ca++) was noted during the 48 h incubation with gallium nitrate compared with controls. Exposure of gallium treated bones to lymphokine, but not PTH caused a significant increase in PGE2 release as previously reported (Bockman, R. S. and Repo, M. A., J Exp Med 154:529, 1981). Prior exposure (48 h preincubation) to 1,5 and 10 mcg/ml gallium nitrate caused a dose dependent decrease in 45-Ca++ release but no significant change in PGE2 release was observed, Table 1.

TABLE 1

| Gallium mcg/ml | $\frac{\text{45-Ca}^{++} \text{ release expt'l}}{\text{45-Ca}^{++} \text{ release control}}$ | | PGE2 (ng/bone) | |
|---|---|---|---|---|
| | PTH | Lymph | PTH | Lymph |
| 0 | 1.21 ± 0.15 | 1.59 ± .1 | 1.4 | 17.1 |
| 1 | 1.24 | 1.54 ± .16 | 2.2 | 17.4 |
| 5 | 1.08 | 1.21 ± .04 | 1.3 | 16.7 |
| 10 | 0.99 | 1.23 ± .04 | 3.9 | 15.1 |
| Control | 1.00 ± .06 | 1.00 ± .06 | 1.2 | 2.0 |

Thus, these results (which demonstrate both intact metabolic function and normal histologic appearance) indicate that the anti-calcium activity of gallium is not mediated through a cytotoxic effect.

C. GALLIUM INCORPORATION INTO BONE MINERAL.

It was found that gallium is directly incorporated into bone material.

In rats treated with gallium nitrate, gallium was incorporated into the bone metaphysis where more active bone mineral turnover was occurring and into the metabolically more active crystalline pool (less calcified matrix). The most striking finding by X-ray diffraction was a marked increase in crystal size in the metaphyseal-derived particles from the gallium treated animals as compared to controls. Conceivably, gallium promotes or stabilizes crystal structure to produce matrix with more crystalline hydroxyapatite, or the drug promotes growth rather than dissolution of smaller crystallites.

D. ANTI-RESORPTIVE EFFECTS OF GALLIUM ON DEVITALIZED BONE

Devitalized bone particles (i.e. bones containing only mineral and matrix without any cellular component) were studied. Such particles from rats tested with gallium nitrate were significantly less susceptible to resorption than controls. This experiment shows that the anti-resorptive effects of gallium are not due to cytotoxic actions upon bone cells.

E. ORAL ABSORPTION OF GALLIUM NITRATE

Summary: As previously noted, the intravenous route has been employed for clinical use. The method of subcutaneous and intraperitoneal injections have been employed in rats.

To evaluate the oral absorption and excretion of gallium nitrate, a concentrated solution of the drug was administered to a dog by oral gavage (total dose=1200 mg). Sequential plasma samples and the next 24 hour urinary volume were collected and assayed for gallium concentration by a flameless atomic absorption sprectrophotometer (Kelsen, D. P. et al, Cancer 46:2009, 1980).

Importantly, the dog sustained no toxic reaction from this treatment whatsoever. The subsequent 24 hour urine volume was 183 ml and it contained a total amount of 1.13 mg of elemental gallium. Assuming similar patterns of excretion in humans and dogs, it is estimated that approximately 0.5–2% of an orally administered dose is absorbed and excreted into the urine. Plasma gallium levels after oral gavage of dog are shown in Table 5.

Table 5: Plasma gallium concentrations in the dog after administration of a single oral dose.

| Time hrs | Gallium Concentration (mcg/ml) |
|---|---|
| 0 | 0 |
| 0.25 | 0.5 |
| 0.5 | 1.25 |
| 1 | 1.37 |
| 2 | 2.75 |
| 4 | 2.0 |
| 24 | 0.75 |

Previous studies (Kelson, D. P. et al, Cancer 46:2009, 1980) have demonstrated that intravenous infusions used in the clinical studies at the dose employed in the clinical studies described below achieve steady-state plasma gallium concentrations which range from 0.9–2.0 mcg/ml. The dog experiment shows that these levels which comprise effective treatment for cancer-related hypercalcemia associated with increased bone resorption are achieved by the oral route. In the preferred embodiment of this invention, administration of gallium 1–4 times per day would be expected to maintain low-level plasma gallium concentrations which are therapeutic for disorders of calcium homeostasis. Extrapolating from the dog data, it is estimated that 0.5–20 gms of gallium nitrate administered orally to a 70 kg human will achieve effective plasma levels. A broader range of gallium plasma levels which are not nephrotoxic is also possible.

CLINICAL STUDIES

F. METABOLIC STUDY OF PATIENTS RECEIVING GALLIUM NITRATE

Summary: Contrary to a previous report in the medical literature (Krakoff, I. H. et al, Cancer 44:1722, 1979), patients who received gallium nitrate in the present studies showed decreased urinary calcium excretion and remained in positive calcium balance while receiving the drug (i.e. retaining more calcium than they excreted). As with most anticancer drugs, gallium can potentially cause serious toxicity. The most serious side-effect being kidney damage. However, studies using sensitive analytical techniques show that nephrotoxicity is generally reversible and that it is not cumulative (Leyland-Jones, B. R. et al, Cancer Treat Rep 67:941, 1983). It has also been found that intermittent high-dose infusions can be administered for 22+ months without serious toxicity. Furthermore, the anti bone-resorptive effects of gallium nitrate are achieved with less than 25-50% of the anticancer dose. Thus the method should retain safety and efficacy for prolonged periods of time.

Experimental Results: Studies of calcium homeostasis require an assessment of multiple factors including dietary intake, excretion of calcium into urine and stool, and analysis of calcium mobilization from body stores (chiefly bone). Four patients who participated in a careful study of the effects of gallium nitrate upon calcium metabolism were thus assessed. Patients were hospitalized and received a diet of defined calcium, sodium, and fluid intake. Measurements of calcium excretion into urine and stool (along with multiple other laboratory tests) were made daily during a 6-day baseline period and during a subsequent treatment period using gallium nitrate. The drug was administered as a continuous infusion at a dose of 300 mg/sq m/day for durations ranging from 4-7 days. Despite the finding that the total serum calcium concentration was reduced by the gallium infusion, we found no significant increase in calcium excretion during the infusion relative to the baseline observation period. These data suggested that gallium nitrate might exert its hypocalcemic effect by directly affecting calcium resorption from bone (Warrell, R. P. Jr, Bockman, R. S. et al, Clin Res 31:511A, (1983)).

G. TREATMENT OF CANCER-RELATED HYPERCALCEMIA WITH GALLIUM NITRATE

Summary: In the initial study, gallium nitrate was used for the treatment of 10 patients with cancer-related hypercalcemia. The daily dose of drug was 200 mg/sq m administered as a continuous infusion for durations ranging from 5-7 days. The diagnoses of this patient population and the change in total serum calcium concentration in response to this therapy are presented in Table 4a. Note that all patients responded to this treatment by a reduction in serum calcium concentration to normal (and frequently sub-normal) values.

With the single exception of Patient 5 (Table 4a), the hypocalcemic effect was not associated with any anticancer effect. Patient 5 demonstrated a transient decrease in the size of a lymphomatous mass followed shortly thereafter by progression of her disease and death. The subsequent increase of her disease was not accompanied by an increase in serum calcium which indicates a persistent control of the metabolic problem despite lack of control of the underlying cancer. All other patients who received the drug manifested progressive cancer despite control of the hypercalcemia. This finding indicates that the hypocalcemic effect is not produced by a direct cytotoxic effect of gallium nitrate upon tumor cells. In a subsequent study, we further reduced the daily dose of gallium nitrate to 100 mg/sq m administered for 5 days. At a lower dose, 5 of 8 patients were normalized (Table 4b). These preliminary clinical results reflect our preclinical studies previously detailed, namely that there exists a distinct dose-response relation to the anti-calcium effect (Warrell, R. P. Jr, Bockman, R. S. et al, J. Clin. Invest. 73:1487 (1984)).

TABLE 4a

Response of patients with cancer-related hypercalcemia to continuous infusion of gallium nitrate (dose = 200 mg/sq m/d × 5-7 d).

| Patient | Cancer Diagnosis | Total Serum Calcium* | |
|---|---|---|---|
| | | Pre-Treatment | Post-Treatment |
| 1 | Breast | 13.8 | 8.9 |
| 2 | Breast | 15.2 | 8.5 |
| 3 | Lymphoma | 15.6 | 6.6 |
| 4 | Head & Neck | 12.3 | 8.5 |
| 5 | Breast | 14.4 | 7.7 |
| 6 | Lymphoma | 15.6 | 8.6 |
| 7 | Lung | 12.5 | 7.0 |
| 8 | Penis | 12.3 | 9.3 |
| 9 | Head & Neck | 13.5 | 7.8 |
| 10 | Lung | 13.7 | 9.3 |

TABLE 4b

Response of patients with cancer-related hypercalcemia to gallium nitrate (dose = 100 mg/sq m/d × 5 d).

| Patient | Diagnosis | Pre-Treatment | Post-Treatment |
|---|---|---|---|
| 1 | Breast | 13.9 | 11.3 |
| 2 | Anus | 12.7 | 6.3 |
| 3 | Kidney | 14.3 | 12.0 |
| 4 | Breast | 14.5 | 8.7 |
| 5 | Pancreas | 14.6 | 10.0 |
| 6 | Myeloma | 15.0 | 13.7 |
| 7 | Lung | 13.0 | 10.8 |
| 8 | Breast | 17.0 | 9.0 |

(*)Serum concentration expressed in mg/dl (normal range, 9.0–10.5 mg/dl).

G. GALLIUM NITRATE DECREASES BONE TURNOVER IN PATIENTS WITH CANCER METASTATIS TO BONE

Summary: Patients with bone metastasis suffer progressive erosion of bone which causes pain, immobilization and fractures. Clinically, bone metastases are evaluated by sequential x-rays over a period of months to years. Other measures have recently been employed to measure bone turnover in patients with both cancer and non-cancerous bone resorption. In general, increased bone turnover is associated with increased loss of calcium into the urine and with increased excretion of hydroxyproline (a component of hydroxyapatite). Measurements of these parameters have been used to assess whether a new drug affects bone resorption (Siris, E. S. et al, New Engl J Med 302:310, 1980). We recently measured these parameters in a patient with multiple myeloma and extensive bone destruction who received gallium nitrate (200 mg/sq m/d × 7 d by infusion).

As shown in Table 6, a marked decrease in the amount of calcium and hydroxyproline excretion was observed, indicating that the drug was effective in reducing bone resorption in this patient. The biochemical improvement was also accompanied by a substantial decrease in bone pain and a reduced requirement for narcotics. There was no effect upon the underlying disease and the patient has since received other chemotherapy for her myeloma.

TABLE 6

Gallium effects on bone turnover.

| Days in Treatment | Urine Volume (ml/24 h) | Calcium (mg/24 h) | Phosphorus (mg/24 h) | OH—Proline (mg/24 h) |
|---|---|---|---|---|
| 1 Previous | 3640 | 618 | 1630 | 95.4 |
| 1 | 4365 | 502 | 567 | 76.0 |

TABLE 6-continued

Gallium effects on bone turnover.

| Days in Treatment | Urine Volume (ml/24 h) | Calcium (mg/24 h) | Phosphorus (mg/24 h) | OH—Proline (mg/24 h) |
|---|---|---|---|---|
| 4 | 3620 | 239 | 607 | 23.9 |
| 8 | 3225 | 97 | 419 | 19.0 |

What is claimed:

1. Method effective against excessive loss of calcium from bone in a human individual requiring such treatment comprising administering to the individual an effective amount of a pharmaceutically acceptable gallium compound.

2. Method of claim 1 wherein said excess loss is due to hypercalcemia.

3. Method of claim 1 wherein said excess loss is due to osteopenia or osteoporosis.

4. Method of claim 1 wherein said excess loss is due to bone metastasis from malignant tumors.

5. Method of claim 1 wherein said excess loss is due to hyperparathyroidism.

6. Method of claim 1 wherein said excess loss is due to periodontal disease and said gallium compound is administered intra-orally in a topical formulation comprising a concentrated rinse, gel or other pharmaceutically acceptable carrier.

7. Method effective against excessive loss of calcium from bone in animals requiring such treatment comprising the administering to said animals of an effective amount of a pharmaceutically acceptable gallium compound.

8. Method of inhibiting release of calcium from bone explants comprising contacting said explants with a gallium compound.

9. Method of claim 1 wherein said gallium compound is administered intravenously, subcutaneously or intramuscularly.

10. Method of claim 3 wherein intravenous injection comprises continuous infusion.

11. Method of claim 9 wherein said injection comprises amount ranging from about 10–400 mg/sq m/day.

12. Method of claim 1 wherein the amount of said administered gallium compound is sufficient to maintain a steady state plasma gallium concentration ranging from about 0.1–5.0 ug/ml.

13. Method claim 12 wherein the amount of said administered gallium compound is sufficient to maintain a steady state plasma gallium concentration ranging from about 0.9–2.0 ug/ml.

14. Method of claim 1 wherein said gallium compound is administered orally, sub-lingually, per rectum or transdermally.

15. Method of claim 14 wherein the amount of administered gallium compound comprises amounts from about 0.5–20 grams/day.

16. Method of claim 1 wherein said gallium compound is selected from the group consisting of gallium nitrate, gallium citrate, gallium halide, gallium chloride, gallium carbonate, gallium acetate, gallium tartrate, gallium oxalate, gallium oxide and hydrated gallium oxide.

17. Method of claim 16 wherein said gallium compound is gallium nitrate.

18. Method of claim 2 wherein said gallium compound is gallium nitrate.

19. Method of claim 3 wherein said gallium compound is gallium nitrate.

20. Method of claim 4 wherein said gallium compound is gallium nitrate.

21. Method of claim 5 wherein said gallium compound is gallium nitrate.

22. Method of claim 6 wherein said gallium compound is gallium nitrate.

23. Method effective against bone pain due to excessive loss of calcium from bone in a human individual requiring such treatment comprising administering to the individual an effective amount of pharmaceutically acceptable gallium compound.

24. Method effective against bone fractures due to excessive loss of calcium from bone in human a individual requiring such treatment comprising administering to the individual an effective amount of a pharmaceutically acceptable gallium compound.

* * * * *

UNITED STATES PATENT AND TRADEMARK OFFICE
CERTIFICATE OF CORRECTION

PATENT NO. : 4,529,593

DATED : July 16, 1985

INVENTOR(S) : Raymond P. Warrell, Jr. et al

It is certified that error appears in the above-identified patent and that said Letters Patent is hereby corrected as shown below:

Column 2, line 39: delete second "in";

line 62: after "intravenous" insert --,--.

Column 3, line 44: change "releases" to --release--;

line 60: change "releases" to --release--.

Column 6, line 17: change "5" to --2--' line 18: change "5" to --2--;

line 61: change "being" to --is--.

Column 7, line 41: change "4a" to --3a--;

line 44: change "4a" to --3a--;

line 62: change "4b" to --3b--.

UNITED STATES PATENT AND TRADEMARK OFFICE
CERTIFICATE OF CORRECTION

PATENT NO. : 4,529,593

DATED : July 16, 1985

INVENTOR(S) : Raymond P. Warrell, Jr. et al

It is certified that error appears in the above-identified patent and that said Letters Patent is hereby corrected as shown below:

Column 8,    change "TABLE 4a" to --TABLE 3a--, and "TABLE 4b" to --TABLE 3b-- line 32: change "G" to --H--;

line 33: change "METASTATIS" to --METASTASIS--;

line 51: change "6" to --4--;

line 61: change "6" to --4--.

Column 9, line 1: change "6" to --4--.

Signed and Sealed this

Twenty-seventh Day of May 1986

[SEAL]

Attest:

DONALD J. QUIGG

Attesting Officer    Commissioner of Patents and Trademarks

UNITED STATES PATENT AND TRADEMARK OFFICE

CERTIFICATE EXTENDING PATENT TERM
UNDER 35 U.S.C. 156

Patent No.    : 4,529,593

Dated         : July 16, 1985

Inventor(s)   : Raymond P. Warrell, Jr. et al

Patent Owner  : Sloan-Kettering Institute for
                Cancer Research

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

915 DAYS with all rights pertaining thereto as provided by 35 U.S.C. 156 (b).

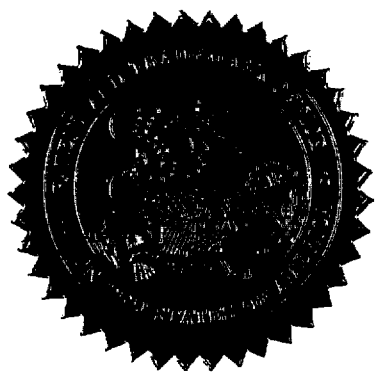

I have caused the seal of the Patent and Trademark Office to be affixed this 30th day of December 1991.

Harry F. Manbeck, Jr.
Assistant Secretary and Commissioner
of Patents and Trademarks